United States Patent [19]

Downer et al.

[11] Patent Number: 4,975,647

[45] Date of Patent: Dec. 4, 1990

[54] CONTROLLING MACHINE OPERATION WITH RESPECT TO CONSUMABLE ACCESSORY UNITS

[75] Inventors: Robert R. Downer, Medfield; Richard C. Noonan, Belmont; David M. Dalke, Marlborough, all of Mass.

[73] Assignee: NOVA Biomedical Corporation, Waltham, Mass.

[21] Appl. No.: 265,836

[22] Filed: Nov. 1, 1988

Related U.S. Application Data

[63] Continuation-in-part of Ser. No. 56,609, Jun. 1, 1987, abandoned.

[51] Int. Cl.$^5$ .................... G01N 27/42; G01N 27/30
[52] U.S. Cl. .................................. 324/425; 204/403; 380/25
[58] Field of Search .................................. 380/23-25, 380/59; 364/185, 413, 415, 551; 239/69, 71; 324/439, 450, 425; 204/401, 403, 406, 442; 422/62, 68, 98, 102

[56] References Cited

U.S. PATENT DOCUMENTS

| | | | |
|---|---|---|---|
| 2,254,329 | 3/1941 | Gokey et al. | 235/379 |
| 3,599,833 | 8/1971 | Reichenberger | 222/23 |
| 3,670,923 | 6/1972 | Hawes, Jr. et al. | 222/2 |
| 3,670,924 | 6/1972 | Asper | 222/2 |
| 3,675,820 | 7/1972 | Newberry et al. | 222/76 |

(List continued on next page.)

FOREIGN PATENT DOCUMENTS

| | | | |
|---|---|---|---|
| 0058472 | 8/1982 | United Kingdom . | |
| 8502257 | 5/1985 | World Int. Prop. O. | 204/412 |

OTHER PUBLICATIONS

Pilarski, Richard, "Recent Trends in Automated Dispensing of Adhesive and Sealants", Rubber World, vol. 192, No. 5, pp. 14-19, Aug. 1985.
"Program Motion Automates Dispensing," Production Engineering, vol. 33, No. 1-6, Jan. 1986, pp. 126-145.
Wurz, "Automatic Identification: A New Code Symbol for Shipping Containers", Material Handling Engineering, pp. 26-29, 1975.
Burke, "Shipping Containers Get a Code of their Own," Material Handling Engineering, Feb. 1976, pp. 53-55.
"Advanced Equipment-For the Production of Flexible Foam Cushion," British Plastics, Aug. 1970, p. 79.

*Primary Examiner*—Salvatore Cangialosi
*Attorney, Agent, or Firm*—Fish & Richardson

[57] ABSTRACT

Apparatus for controlling the use of consumable accessory units with machines where a memory device associated with each accessory unit holds information concerning the accessory unit, and circuitry in the machine acts in response to the information. The information includes (1) the classes of machines with which the accessory unit is intended to be used (the machine issues a signal if the machine is not within one of the intended classes); (2) the concentration of the contents of the accessory unit (the machine operation is controlled on the basis of the concentration); (3) an encrypted authorization code (the machine issues a signal if the decrypted code is not an authorized one); (4) the manufacturing lot the accessory unit (the machine displays the lot number to the user); (5) the expiration date of the accessory unit (the machine issues a signal if the expiration date has passed); (6) a unique identification number to trigger the machine to compare a predetermined total number of permissible uses with the number of actual uses (the machine issues a signal when the accessory unit is deemed to be empty); (7) information concerning calibration of the machine (the electronic circuitry is calibrated in response to the information); (8) the range of permissible operating conditions for the machine in conjunction with the accessory unit (the machine displays the information for operator use); (9) the range of permissible use of the accessory unit (the machine displays the permissible uses to the operator); and (10) the range of permissible quantities of material that may be added to the accessory unit (the machine displays the information to the user).

25 Claims, 10 Drawing Sheets

U.S. PATENT DOCUMENTS

| | | | |
|---|---|---|---|
| 3,688,947 | 9/1972 | Reichenberger | 222/27 |
| 3,877,645 | 4/1975 | Oligschlaeger | 239/155 |
| 3,920,149 | 11/1975 | Fortino et al. | 222/1 |
| 4,006,396 | 2/1977 | Bogut | 320/2 |
| 4,023,020 | 5/1977 | Lestradet | 235/151.2 |
| 4,034,757 | 7/1977 | Glover | 128/260 |
| 4,039,933 | 8/1977 | Moran | 324/425 |
| 4,044,227 | 8/1977 | Holm et al. | 235/61.7 |
| 4,052,003 | 10/1977 | Steffen | 239/71 |
| 4,136,503 | 1/1979 | Miller | 53/507 |
| 4,220,998 | 9/1980 | Kays | 364/510 |
| 4,234,926 | 11/1980 | Wallace et al. | 364/185 |
| 4,248,389 | 2/1981 | Thompson et al. | 241/101.5 |
| 4,266,262 | 5/1981 | Haase, Jr. | 361/228 |
| 4,272,019 | 6/1981 | Halaby, Jr. | 239/8 |
| 4,275,846 | 6/1981 | Coffee | 239/690 |
| 4,317,030 | 2/1982 | Berghell | 235/489 |
| 4,317,957 | 3/1982 | Sendrow | 380/24 |
| 4,358,059 | 11/1982 | coffee | 239/691 |
| 4,364,472 | 12/1982 | Waldmeier | 206/45.34 |
| 4,386,266 | 5/1983 | Chesarek | 380/25 |
| 4,401,274 | 8/1983 | Coffee | 239/690 |
| 4,411,351 | 10/1983 | Lowder et al. | 194/4 |
| 4,467,961 | 8/1984 | Coffee et al. | 239/71 |
| 4,500,750 | 2/1985 | Elander et al. | 380/24 |
| 4,535,557 | 8/1955 | Porcher | 235/487 |
| 4,553,702 | 11/1985 | Coffee et al. | 239/71 |
| 4,578,530 | 3/1986 | Zeidler | 380/24 |
| 4,580,721 | 4/1986 | Coffee et al. | 239/3 |
| 4,629,164 | 12/1986 | Sommerville | 239/71 |
| 4,654,127 | 3/1987 | Baker et al. | 204/401 |
| 4,686,479 | 8/1987 | Young et al. | 324/439 |
| 4,691,350 | 9/1987 | Kleijne et al. | 380/23 |
| 4,695,954 | 9/1987 | Rose et al. | 364/413 |
| 4,739,238 | 4/1988 | Koelle et al. | 342/51 |
| 4,799,635 | 1/1989 | Nakagawa | 364/900 |
| 4,802,218 | 1/1989 | Wright et al. | 380/23 |

230 {
  Column Type
    Inner Diameter
    Length
    Material
    Packing Active Component
    Packing Support Component
}

232 {
  Classes Of Compounds
    Primary
    Secondary
}

234 { Lot Number

236 { Date

238 {
  Conditions For Use
    For Gas Chromatography
      Flow Rates Range
      Injector Temperature Range
      Oven Temperature Range
      Detector Temperature Range
}

For Liquid Chromatography
    Eluent Types
    Pressure Range Or Maximum
    Regeneration Internal
    Temperature Range 240 { Sample Sizes 242 { Calibration

FIG. 9

CONTROLLING MACHINE OPERATION WITH RESPECT TO CONSUMABLE ACCESSORY UNITS

This application is a continuation-in-part of U.S.S.N. 056,609, filed June 1, 1987, now abandoned.

BACKGROUND OF THE INVENTION

This invention relates to storing information about the contents of a consumable accessory unit in a storage device associated with the unit, and then taking some action related to the unit or its contents based on the stored information.

It is known to incorporate a read only memory (ROM) into a container for storing information. In Coffee et al., U.S. Pat. No. 4,580,721, issued Apr. 8, 1986, the container holds a pesticide, and the ROM stores the following information (col. 13, lines 31-64, and Table II): a "handshake security code" to restrict usage of the container; "acceptable flow rates" for the pesticide; a "voltage" setting for an electrostatic sprayer for the pesticide; the "container size;" the "chemical type" of the pesticide; and "the formulation date." Coffee also uses a programmable ROM in the container to hold and update a value representing the "liquid quantity" in the container. Coffee s container is used with spray machinery that includes electronics which control the spraying of the pesticide based on the information in the ROM.

SUMMARY OF THE INVENTION

The general features of the invention relate to controlling the use of consumable accessory units with machines (e.g., analytical machines or chromatographs) where a memory device associated with each accessory unit contains information concerning the unit, its contents, or the manner in which it is to be used, and circuitry in the machine acts in response to or displays the information.

In one general feature of the invention, the machines comprise at least one of a plurality of different classes of machines adapted to receive consumable accessory units, each machine being arranged to take some action with respect to the contents of the accessory unit; the memory device stores information indicative of the predetermined classes of machines with which the accessory unit is intended to be used; and the machine circuitry issues a signal when the stored information indicates that the machine is not within those predetermined classes.

In another general feature of the invention, the machine performs an operation (e.g., a calibration operation) that depends on the concentration of the contents of a consumable accessory unit associated with the machine; the memory device holds information stating the concentration; and the machine circuitry controls the operation based on the concentration information.

In another general feature of the invention, the memory device holds information indicative of whether or not the accessory unit is authorized for use, the information being encrypted in accordance with a predetermined encryption scheme; the machine circuitry decrypts the information in accordance with the predetermined encryption scheme and issues a signal if the decrypted information indicates that the accessory unit is not an authorized one.

In another general feature of the invention, the memory device holds information indicative of the manufacturing lot of the accessory unit; the machine circuitry reads the information from the memory device and displays the information to a user of the machine.

In another general feature of the invention, the memory device holds information indicative of the expiration date of the accessory unit; the machine circuitry issues a signal when the expiration date has passed.

In another general feature of the invention, the memory device holds information uniquely identifying each accessory unit; the machine circuitry holds information indicative of the predetermined total number of possible uses, keeps track of the total number of uses of the accessory unit, and issues a signal when the total number of uses equals the predetermined total number.

In another general feature of the invention, for controlling the use of consumable accessory units with a machine for measuring a parameter where the machine requiring calibration, the memory device contains information concerning the timing of the calibration of the machine, and the machine circuitry controls the timing of the calibration based on the information.

In another general feature of the invention, the memory device contains information indicative of a range of permissible operating conditions for the machine in conjunction with the accessory unit, and the machine circuitry reads the information from the memory device and displays it to a user of the machine.

In another general feature of the invention, the memory device contains information indicative of a range of permissible uses for the accessory unit, and the machine circuitry reads and displays the information to the machine user.

In another general feature of the invention, the memory device contains information indicative of a range of permissible quantities of material that may be added to the accessory unit, and the machine circuitry reads and displays the information to the machine user Preferred embodiments include the following features. The memory device is a ROM that is connected electrically to the machine circuitry, and is permanently physically connected to the accessory unit by a tether. The circuitry includes a microprocessor controlled by a stored program. The machine is a blood analyzer, and the accessory unit holds electrolyte solution fluids for use in calibrating the circuitry (and associated sensors) in connection with performing blood analysis. The information concerning the timing of the calibration includes a value indicative of a time interval following a calibration after which another calibration will be considered. The information concerning the timing of calibration includes a value indicative of the frequency with which calibrations are to be performed relative to the frequency with which the machine makes measurements of the parameter. Alternatively, the machine is a gas or liquid chromatography device, and the accessory unit is a chromatography column for use in conjunction with the device. When the circuitry issues one of the signals (for example, when the container is not intended for use on the machine), the accessory unit is prevented from being used on the machine.

The invention also features the consumable accessory unit itself, where the memory is arranged to be automatically read by the machine.

In preferred embodiments, the accessory unit has one or more chambers for holding substances and the memory device is attached to the chambers.

The invention insures that the correct fluids pack or column is installed in the machine; warns the user if the expiration date has passed; keeps track of how many uses remain for the fluids pack or column; prevents the user from attempting to use an empty fluids pack; ensures that the fluids pack will work properly with the analyzer even when the electrolyte concentrations are changed from the concentrations used in other packs; prevents the use of unauthorized fluids packs or columns; and enables the manufacturer of the packs to chance the concentrations or the manufacturer of the columns to change the calibration without having to change the software in the machine.

Other advantages and features of the invention will become apparent from the following description of the preferred embodiments and the claims.

DESCRIPTION OF THE PREFERRED EMBODIMENTS

We first briefly describe the drawings.

DRAWINGS

FIG. 9 is a table of information that may be stored in the PROM pod for a chromatography column

STRUCTURE

Figure 1:
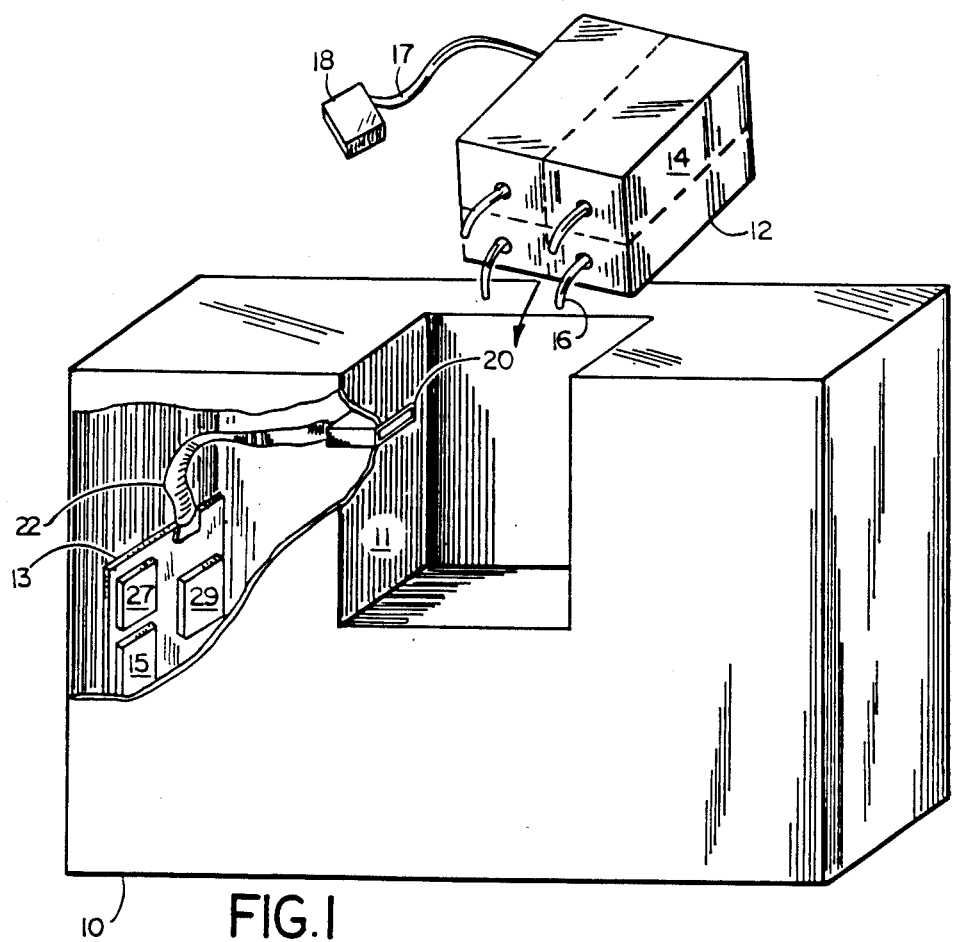
FIG. 1 is an isometric view of a fluids pack about to be inserted into a blood analyzer.

Referring to FIG. 1, a blood analyzer 10 (of the kind described in Young et al., U.S. Pat. No. 4,686,479, issued Aug. 11, 1987 (assigned to the same assignee as this invention) has a bay 11 for holding a replaceable fluids pack 12. Four standard electrolyte solutions stored in four separate chambers 14 of fluids pack 12 are used to calibrate electronic circuitry 13 in connection with analyzing blood samples. The chambers 14 of fluids pack 12 are connected to analyzer 10 respectively via four fluid connections 16.

The four electrolyte solutions comprise two pairs, each pair containing two different concentrations of the same electrolyte (as required to calibrate electronic circuitry 13).

Information about pack 12 and the electrolyte solutions is stored in a fluids identification (FID) pod 18. A plastic tether 17 is securely attached at one end to FID pod 18 and at its other end to fluids pack 12. When fluids pack 12 is installed in analyzer 10, FID pod 18 is plugged into a FID pod connector 20. A cable 22 electrically connects FID pod 18 to electronic circuitry 13. Circuitry 13 includes at least one microprocessor 15 (with software in a programmable EPROM 29) which, among other things, fetches, processes and acts in response to the information stored in FID pod 18. Circuitry 13 also includes an electrically erasable programmable read-only-memory (EEPROM) 27, having 8,192 bytes of storage. EEPROM 27 holds information about the usage of pack 12 and is written and read by microprocessor 15.

Figure 2:
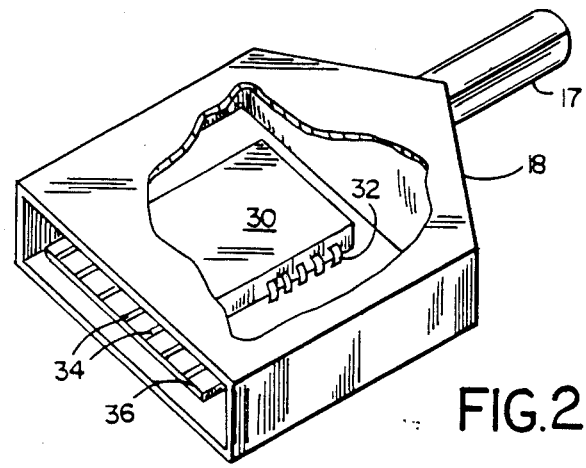
FIG. 2 is an isometric view of the fluids identification pod of FIG. 1 partially broken away.

Referring to FIG. 2, FID pod 18 contains a FID programmable read-only memory (PROM) 30 whose pins 32 are electrically connected to fingers 34 arranged along one edge of a printed circuit board 36. Fingers 34 make electrical contact with a corresponding set of contacts in connector 20.

PROM 30 is a 1024-bit bipolar PROM, programmed during the manufacturing process, whose storage is divided into 256 four bit nibbles. The four-bit nibbles are arranged by pairs into 128 eight-bit bytes with even nibbles forming the high order four bits of each byte and odd nibbles forming the low order four bits of each byte. The 128 bytes are divided into two 64-byte sections which each contains a complete copy of the data stored within PROM 30. (The second copy of the data provides redundancy to reduce the chances of data loss.) A suitable data organization within each 64-byte section is as follows:

| Byte  | Function                          |
|-------|-----------------------------------|
| 0     | Analyzer Type                     |
| 1-7   | Lot Number                        |
| 8     | Expiration Date, Month            |
| 9     | Expiration Date, Year             |
| 10-13 | Fluids Pack Number                |
| 14-61 | Fluids Pack Concentrations        |
|       | Zone 1 Calibration Time           |
|       | Zone 2 Calibration Time           |
|       | Calibration Slippage Variable     |
|       | for Analysis                      |
|       | Calibration Slippage Variable     |
|       | for Calibration                   |
| 62-63 | Checkword                         |

Byte 0 contains a binary number from 0 to 255 which identifies the type of blood analyzer 10 with which this fluids pack is intended to be used. Bytes 1–7 together form a string of ASCII (American Standard Code for Information Interchange) characters identifying the manufacturing lot to which the contents of the fluids pack belong. Byte 8 identifies the final month after which the contents of the fluids pack are deemed to have expired. Byte 9 identifies the year of expiration. Bytes 10–13 contain a 24 bit fluids pack number (FPN), i e., a serial number (ranging from 1 to 16,777,215) which uniquely identifies the pack among all others to be used with the type of analyzer designated in byte 0. The FPN is stored in an encrypted format which uses all 32 bits of bytes 10–13. Bytes 14–61 are used to store various parameters, including the respective concentrations of the electrolyte solutions, the calibration zone times and the slippage variables. Finally, bytes 62–63 contain a conventional two-byte CRC-16 checkword calculated from the other sixty two bytes and capable of detecting more than 99% of all errors in the data.

Figure 3:
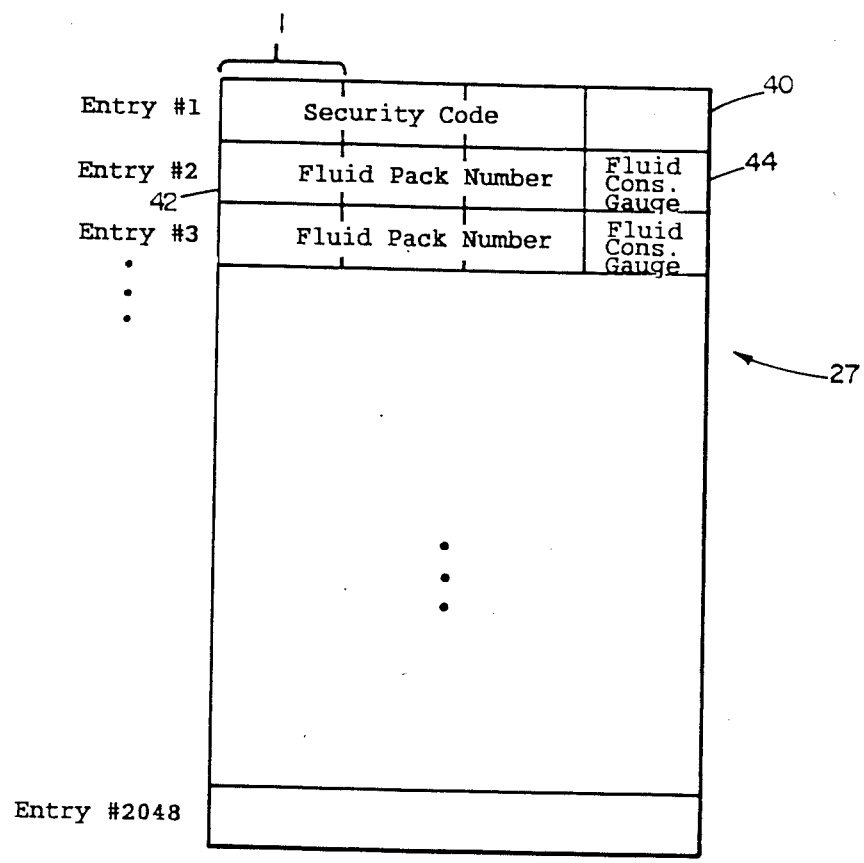
FIG. 3 is a diagram of the contents of an EEPROM of the blood analyzer of FIG. 1.

Referring to FIG. 3, the 8,192 bytes of storage contained within EEPROM 27 are organized as 2,048 four-byte entries. The first entry in EEPROM 27 contains a security code 40. Each succeeding entry is arranged to store a three-byte decrypted FPN 42 and an associated one byte fluid consumption gauge number (FCG) 44 for a given fluids pack that has been or is being used on analyzer 10.

When a new fluids pack is first used with the analyzer, its FPN is stored in the next available entry in EEPROM 27 and its associated FCG 44 is set to 255 (to indicate that the fluid pack is full). Each time the fluids in the pack are used, the FCG is updated to reflect the number of uses of fluids remaining such that when the fluid pack is deemed to be empty, its FCG will equal 0.

To determine the next available entry for a new fluids pack, EEPROM 27 is scanned to locate the first blank entry. Each time an FPN is stored, the next entry is cleared, and becomes the next available entry. After the last entry (2048) has been filled, the next FPN is stored in the second entry and EEPROM 27 contains the FPN's of the previous 2047 fluid packs used with the analyzer.

OPERATION

During operation of blood analyzer 10, as part of each blood analysis performed, the electronic circuitry 13 and associated sensors (not shown) are calibrated using electrolyte solutions drawn from fluids pack 12. The accuracy of the calibration operation requires that circuitry 13 know the true concentration values for the solutions contained in each pack and also requires that electrolyte solutions which have not been properly prepared or which no longer retain their potency not be used. To this end, the system software contained in the analyzer 10 includes procedures which, from time to time during the operation of the analyzer, use the information contained in FID PROM 30 to determine (1) the concentration values and to verify that (1) the EEPROM 27 contains valid information; (2) the pack is intended for use with the type of analyzer in which it is installed; (3) the fluids in the pack are not being used beyond their expiration date; (4) the pack is not deemed to be empty; and (5) the data stored in FID PROM 30, on which these other procedures are based, has not been corrupted.

Figure 4:
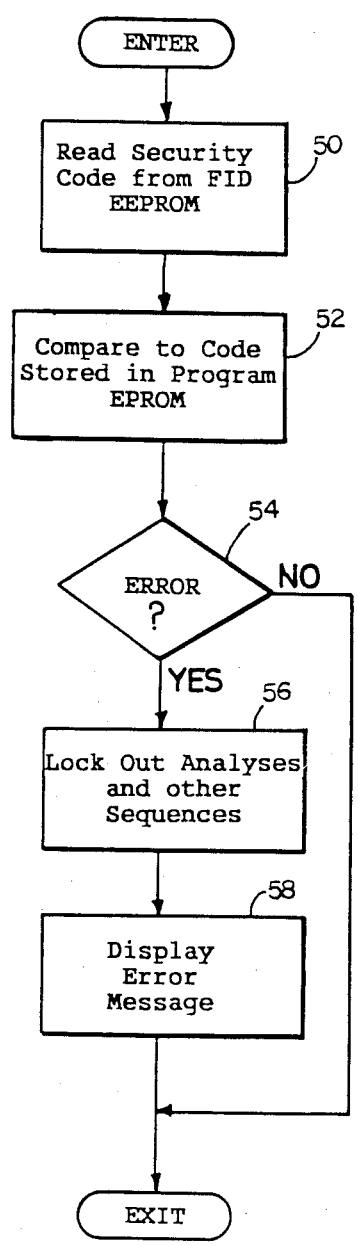
FIGS. 4, 5A–5D and 6 are flow charts respectively describing the "check EEPROM security code," "read ROM cartridge and update EEPROM," and "update fluid consumption gauge" routines of the software controlling the blood analyzer of FIG. 1.

Specifically, referring to FIG. 4, when analyzer 10 is powered-up or reset, the security code 40 stored in EEPROM 27 is read (50) and compared (52) to the code value stored in the program EPROM 29, to assure that the EEPROM contains valid information. If the codes are not equal, an error condition (54) is indicated, all further analyses and other sequences are locked-out (56), and an appropriate error message is displayed (58) on screen 31. If, conversely, the codes are equal, the analyzer is activated for use.

Whenever analyzer 10 is turned on or reset, whenever each analysis, calibration, or other sequence is begun, and whenever a new fluids pack is installed in the analyzer, the information in FID PROM 30 is read and verified, and the information in EEPROM 27 may be updated in the following manner.

Referring to FIGS. 5A, 5B, 5C, 5D, the entire first copy of bytes 0 through 61 of data stored in FID PROM 30 is read (60), and the checkword for those bytes is computed (62). If the computed checkword does not equal (64) the checkword originally stored in bytes 62-63, then the first copy of the data is discarded and the second copy of the data is read (66) from PROM 30. A checkword is calculated (68) for this data and compared (70) with the checkword stored in bytes 62-63 in the second copy of the data. If the checkwords are again unequal (72), the user is locked out (74, FIG. 5D) from performing any further analyses using the pack, and an appropriate error message is displayed (76, FIG. 5D) indicating that both copies of the data in the FID PROM 30 are wrong.

If, however, one or the other of the copies of the data is valid (78, 80) (that is, the computed checkword equals the stored checkword for that copy of the data), then the analyzer type (stored at byte 0) is compared to the actual analyzer type (stored in the program EPROM 29) (82). If the analyzer type is not correct (84), a lock out occurs (74), and an appropriate error message is displayed (76).

Figure 5A:
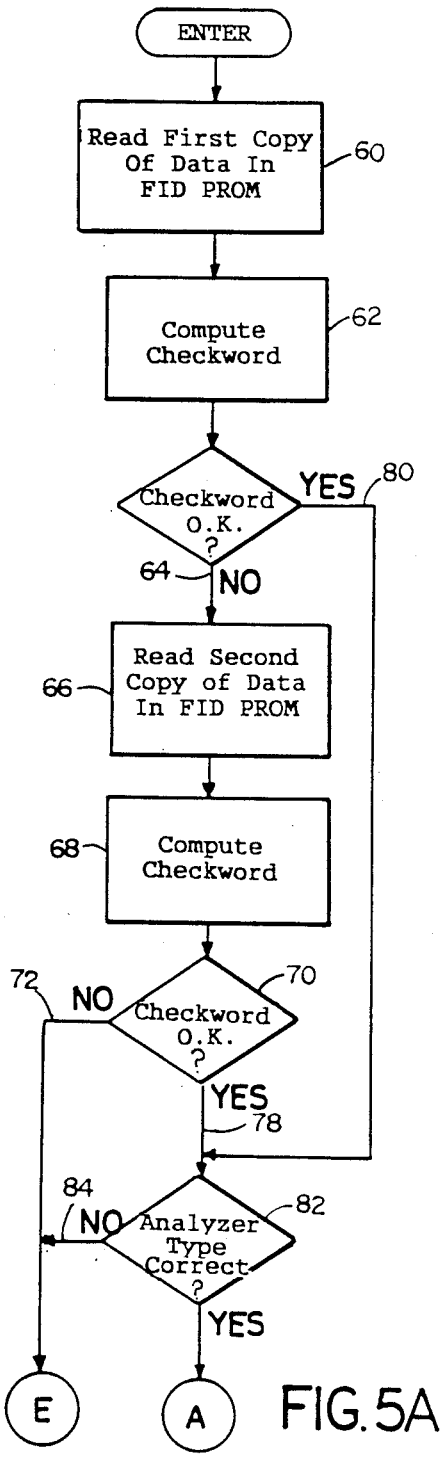
Figure 5B:
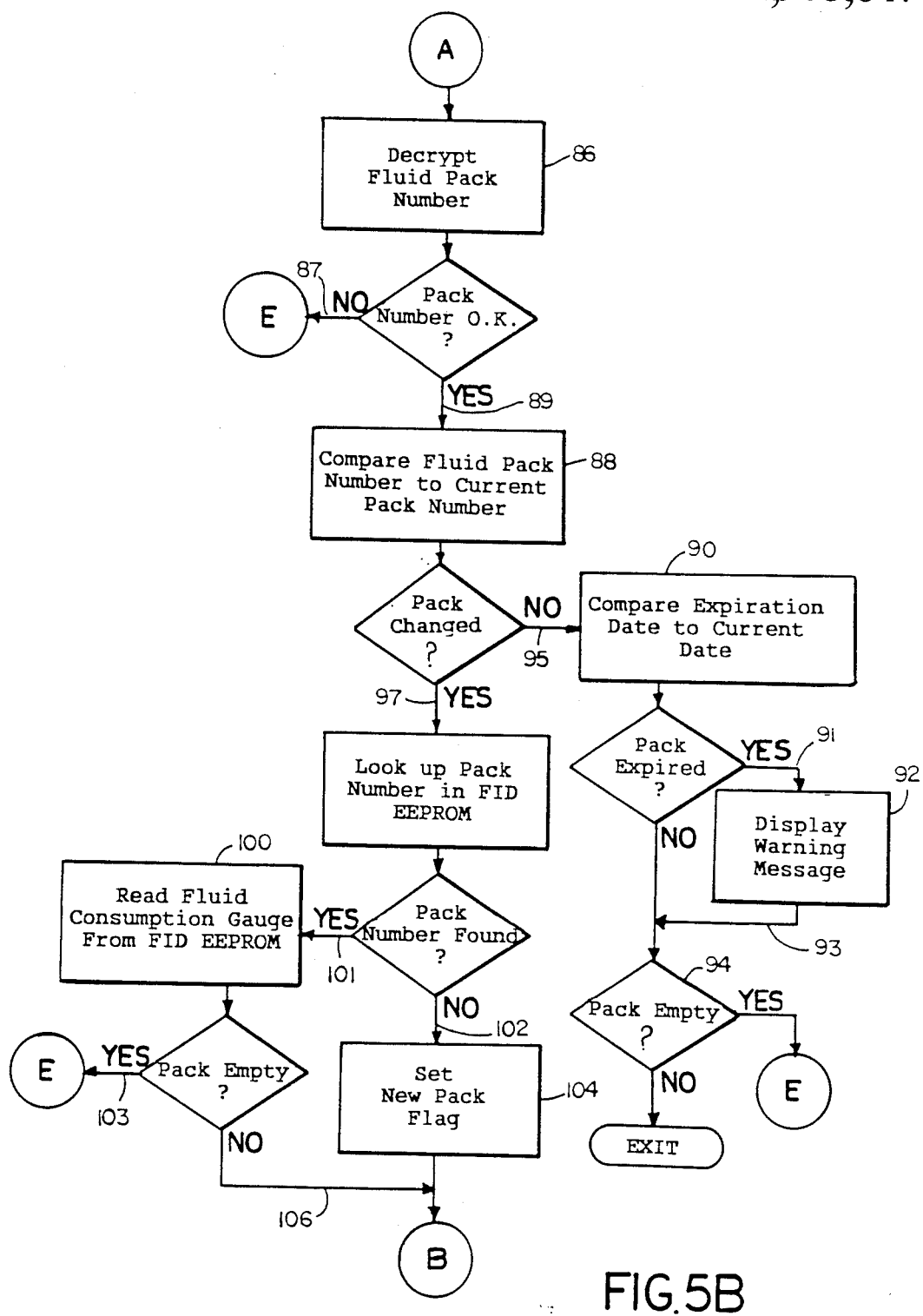
Figure 5C:
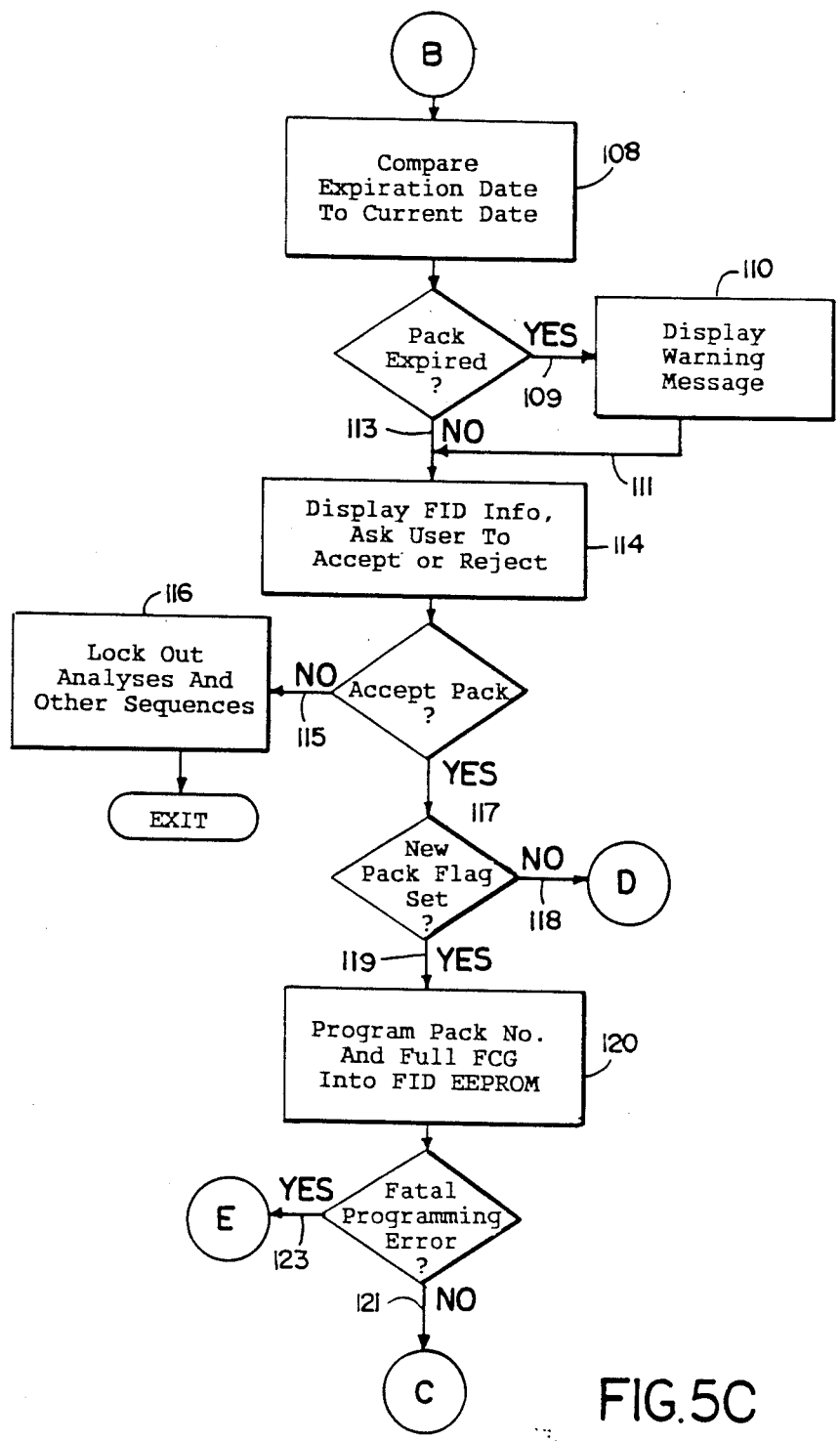
Figure 5D:
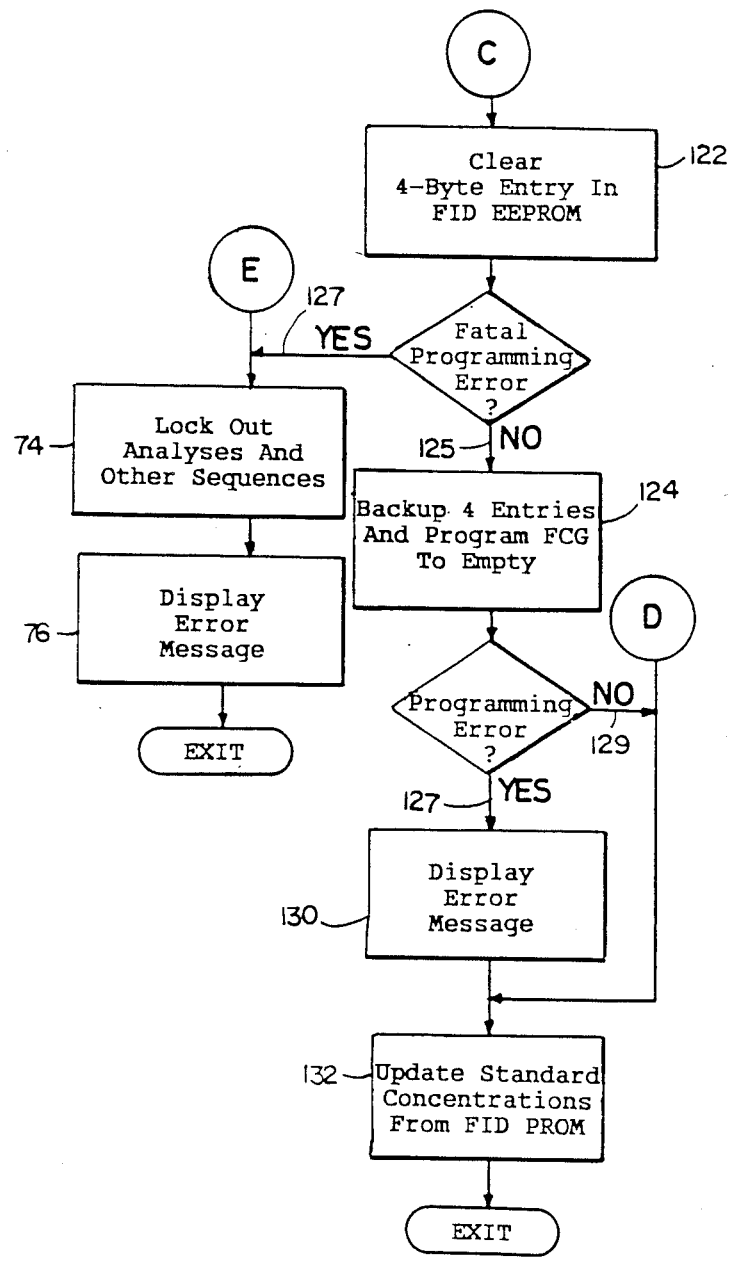

If the analyzer type is correct, the FPN 44 stored in bytes 10-13 is decrypted (86), by a method that depends on the analyzer type. Referring to FIG. 5B, if decryption does not yield a valid FPN (87), lock-out occurs (74), and an appropriate error message is displayed (76). If decryption does yield a valid FPN (89), it is compared (88) to the current pack number (CPN) (i.e. the FPN of the pack used in the most recently performed analysis and stored in electronic circuitry 13); if they are equal, the pack has not been changed since the previous performance of the verification procedure.

If this is so (95), the expiration date (month/year) stored in bytes 8-9 is compared (90) to the current date to determine whether the pack has expired. If the current date is later than the expiration date (91), a warning message is displayed (92), and the user is given the option of proceeding or not; if the user chooses to proceed (93), the EEPROM entry 44 corresponding to the fluids pack is checked to see if the pack is to be construed as being empty, if it is, a lock-out occurs (74), and an appropriate error message is displayed (76); if it is not, the verification procedure has been completed, and the blood analysis can proceed.

If, on the other hand, the FPN is not equal to the current pack number (97), then the fluids pack has been changed since the previous performance of the verification procedure. If this is the case, the FPN retrieved from the FID PROM is compared with the FPNs stored in EEPROM 27 to determine whether this pack has previously been used with this analyzer. If it has (101), the FCG associated with the FPN is read from the EEPROM (100). If it indicates (103) that the fluids pack is to be construed as empty (see description below), lock-out occurs (74), and an appropriate error message is displayed (76).

If the FPN retrieved from the FID PROM is not found in the EEPROM (102), a new pack flag is set (104) which will result in writing a new FPN later (at 120).

If either the FPN was found in EEPROM 27 and the fluid pack was not empty (106), or the FPN was not found (102), the expiration date stored in bytes 8-9 is compared to the current date (108, FIG. 5C), and, if the pack has expired (109), a warning message is displayed (110).

If either the pack has expired and the user nevertheless chooses to proceed (111) or the pack has not expired (113), all of the pertinent information derived from the FID PROM and the EEPROM is displayed, and the user is asked to accept or reject the fluid pack (114). If he does not accept the pack (115), a lock-out occurs (116), and the verification procedure terminates unsuccessfully.

If the user does accept the pack (117) and if the new pack flag is set (119), the FPN and its associated FCG are stored in the next available entry in EEPROM 27 (120). If the new pack flag is not set (118), the next step is to update standard concentrations (132). If the storage operation is successful (121) (if it is not (123), a lock out occurs), the next entry in EEPROM 27 is cleared (122, FIG. 5D). If this entry is successfully cleared (125) (if it is not (127), a lock-out occurs), the FCG in the fourth entry behind the current entry is set to zero (i.e., empty). If this final operation on EEPROM 27 is successful (129) (if it is not (1270), an error message is displayed — 130), the concentration values of the electrolyte solutions stored in the electronic circuitry 13 are updated (132) with the values stored in bytes 14–61 in the FID PROM data for use in calibrating the electronic circuitry.

Figure 6:
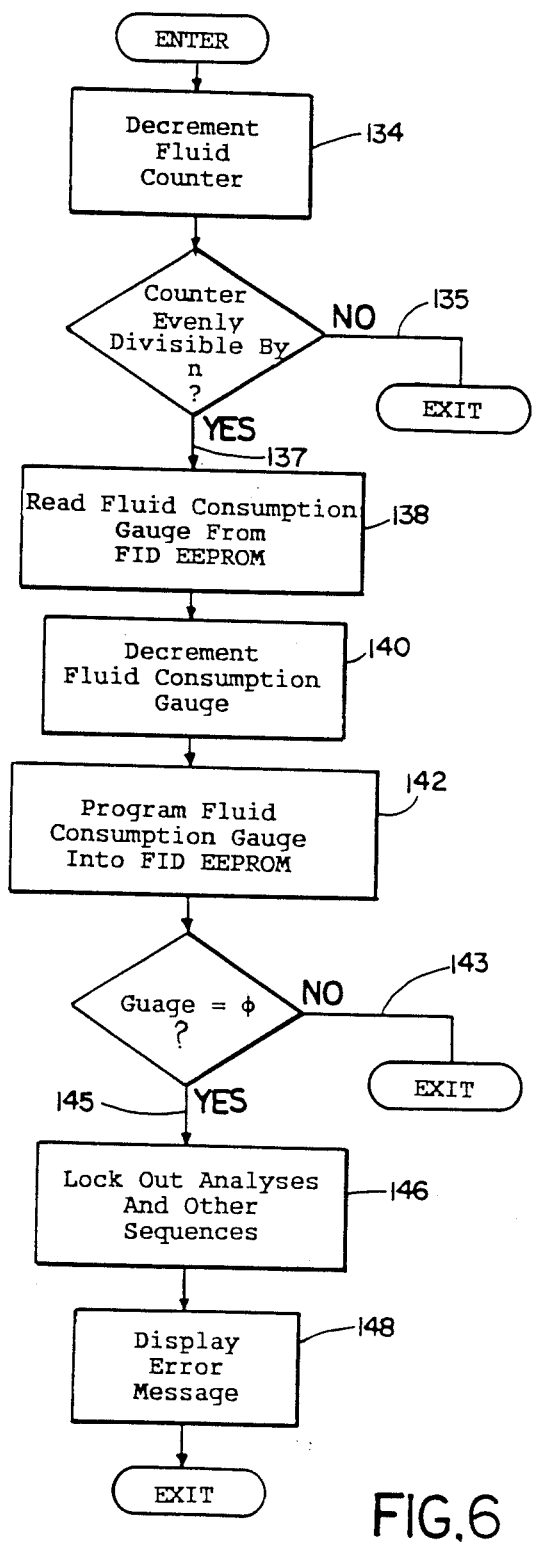

Referring to FIG. 6, during the lifetime of a fluids pack, its FCG must be updated as its fluids are consumed This is done by maintaining a fluid counter (in the electronic circuitry 13) which is decremented each time an analysis is performed, i.e., a unit of fluids is consumed (134). The FCG has the capacity to resolve only 256 fluid levels, but a fluids pack may be designed to yield more than 256 analyses. Therefore, the FCG is not necessarily decremented each time the fluid counter is. Instead, a ratio, n, between the volume of the fluids pack and the capacity of the FCG is calculated. After the counter is decremented, a check is made to determine if the current value of the counter is evenly divisible by n; if it is not (135), the update procedure terminates. If it is (137), then the FCG associated with the FPN is read (138), decremented by one (140), and restored in EEPROM 27. If the gauge does not equal zero (143), the update procedure terminates. If the gauge has reached zero (145), indicating that the fluid's pack is construed to be empty, a lock-out (146) occurs, and an appropriate error message is displayed (148). Note that the total number of possible uses of the pack counted by the fluids counter is only an estimate of when the fluids pack will be actually empty, based on the estimated amount of fluids used per analysis. When the counter reaches zero, there may still be a small amount of fluids remaining in the pack.

The analyzer also includes a feature to manage the frequency and times at which the analyzer is calibrated using the calibration fluids. By deferring calibration during periods when the module is not performing analyses, the rate of use of calibration fluids is reduced. In particular, the cost of the fluids per analysis tends to be equalized as between high and low volume (measured by number of analyses per day) users.

In the invention, calibration is triggered based on three conditions: (1) whether the analyzer is receiving requests to perform analyses, (2) the chemical stability of the fluids, and (3) the elapsed time since the previous calibration.

In general, analyzer 10 slips out of calibration (i.e., defers performing further calibrations) if more than a certain period of time has elapsed since the previous calibration and the analyzer has received no requests for analysis during that period. Slipping conserves fluids by reducing the frequency of calibrations; if the analyzer is not performing analyses, it is assumed not to need calibration.

Analyzer 10 includes software that allows the analyzer to slip automatically out of calibration mode based on defined calibration mode time zones (Zone 1, Zone 2, and Zone 3). The period of time the analyzer can spend in each of Zones 1 and 2 is stored in the PROM as Zone 1 Calibration Time and Zone 2 Calibration Time. For example the Zone 1 and Zone 2 calibration times may be 2 hours and 6 hours respectively. The analyzer shifts among the three zones based on the time elapsed since the last calibration and on the value of a Calibration Slippage Counter The counter (stored in the analyzer) is (a) initialized to zero, (b) upon each analysis operation is incremented by the value of the Calibration Slippage Variable for Analysis (stored in the PROM; typical value is, e.g., 1), and (c) upon each calibration operation is decremented (but never below zero) by the value of the Calibration Slippage Variable for Calibration (also stored in the PROM; typical value is, e.g., 3).

Figure 7:
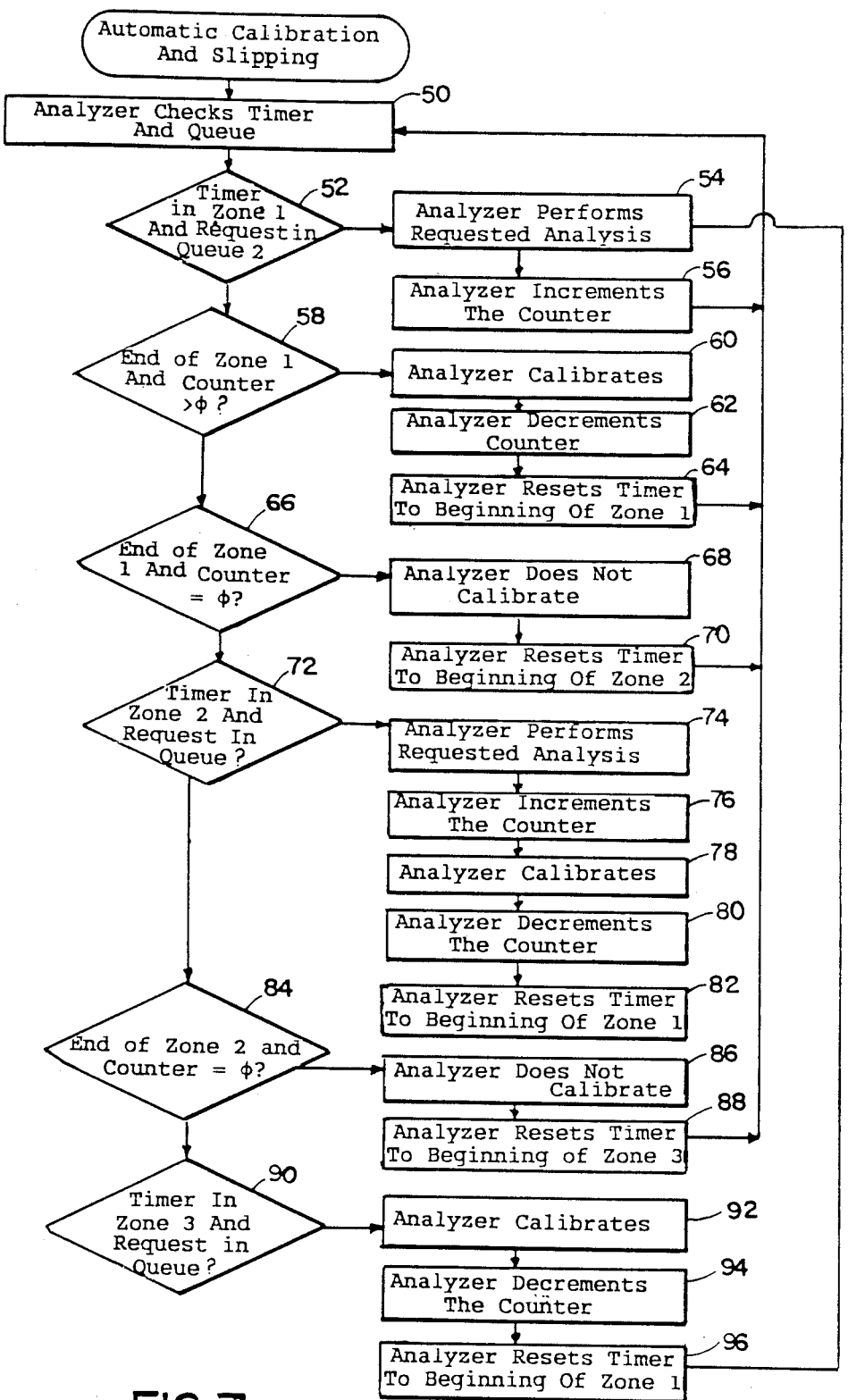
FIG. 7 is a flow chart of a calibration control routine.

Referring to FIG. 7, specifically, in the Automatic Calibration Slipping Routine, a timer in the analyzer keeps track of the time elapsed since the previous calibration and a queue in the analyzer stores requests for a test to be performed. The analyzer continually checks the timer to see which time zone is in effect and checks the queue for any pending requests.

When operating in Zone 1, the module is fully calibrated and normal analyses may be performed. The analyzer stays in Zone 1 until the Zone 1 Calibration Time has elapsed. While the timer is within Zone 1 (52), the analyzer performs any requested analysis 54, increments the counter 56 by the Calibration Slippage Variable for Analysis, and returns to check the timer and queue.

At the end of Zone 1, if the analyzer has performed one or more analyses 58, i.e., fluids have been used and hence the counter is greater than zero, the analyzer immediately calibrates 60, decrements the counter 62, resets the timer to zero, indicating the beginning of the Zone 1 period 64, and returns to check the timer. If, however, at the end of the time allotted for Zone 1, there have been no analysis requests 66, i.e., fluids have not been used and hence the counter remains at zero, the analyzer does not calibrate 68, zeroes the timer to indicate the beginning of the Zone 2 period 70, and returns to check the timer Of course, the counter could still be greater than zero if it entered the most recent Zone 1 time period at a value greater than zero and in that case a calibration would be performed and the routine would return to begin a new Zone 1 time period. Further, if any of the instability conditions described below occurs during the time allotted for Zone 1, the analyzer immediately calibrates and returns to the beginning of the Zone 1 period.

When operating in Zone 2, the analyzer is fully calibrated but normal analysis is not allowed. In Zone 2, if the analyzer receives an analysis request 72, it performs the analysis with single point correction 74, and increments the counter 76 by the value of the Calibration Slippage Variable for Analysis. The analysis causes the analyzer to immediately calibrate 78 and to decrement the counter 80. Because the analyzer was just calibrated, it resets the timer to the beginning of the Zone 1 period 82, and returns to check the timer. If, however, there are no analysis requests during the Zone 2 time period 84, the module does not calibrate 86, resets the timer to the beginning of the Zone 3 period 88, and returns to check the timer. Further, if any of the chemical instability conditions described below occurs during the time allotted to Zone 2, the analyzer slips into Zone 3.

In Zone 3, the analyzer is uncalibrated and no analysis is allowed. The Zone 3 period 90 continues indefinitely until an analysis is requested The analyzer must perform at least one calibration 92 before it can perform the analysis. Multiple calibrations may be necessary and if so are done automatically.

In Zone 3, if the time since the last calibration is within acceptable limits and the slope of the calibration curve is acceptable, then only one calibration is necessary. Otherwise, at least two calibrations are necessary and they must pass acceptable slope requirements. Once the analyzer is calibrated, it decrements the counter 94, resets the timer to the beginning of the Zone 1 period 96, and returns to check the timer.

Automatic calibration slipping will also be enabled after 24 hours of the analyzer being analytically idle, regardless of the counter value, thus conserving fluids. Among the instability conditions that may trigger automatic recalibration, regardless of the counter value, are: excessive Standard A drift, excessive temperature drift, and flow rate changes. All of these conditions are checked continuously by software in the analyzer 10.

Because it is the values stored in the PROM which control the calibration routine, the manufacturer of the fluids packs can control the calibration operations of the machine. The calibration counter has the effect of conserving fluids in low volume usage machines while maintaining calibration in high volume usage machines.

The invention helps to prevent a fluids pack from being used on a wrong analyzer, or used after it has expired, or used at all if it has an invalid serial number or its PROM data is corrupted, and reduces the use of calibration fluids. Accurate calibrations of the electronic circuitry are achieved. Use of the pack is prevented after the pack is deemed to be empty.

Other embodiments are within the following claims.

Figure 8:
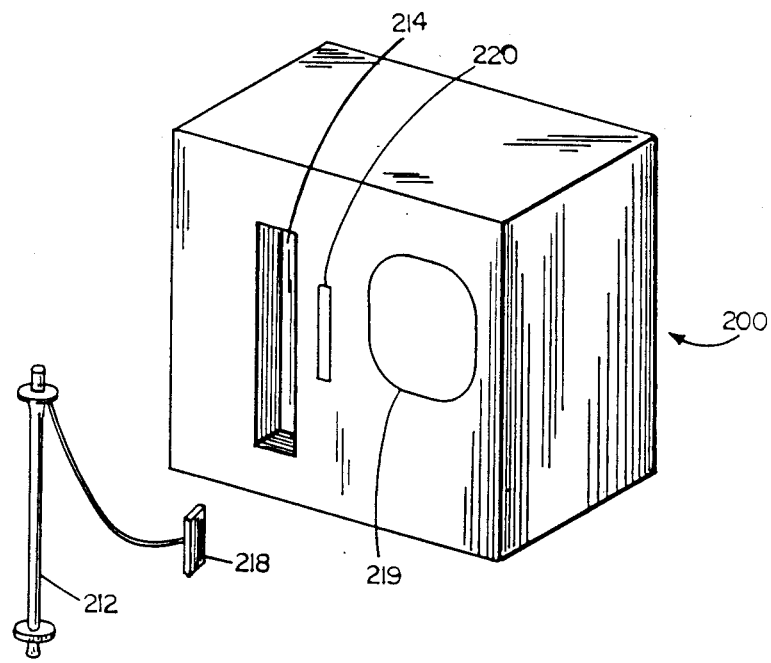
FIG. 8 is an isometric view of a chromatography column about to be installed in a chromatograph.

For example, referring to FIG. 8, in an analogous fashion a disposable chromatographic column 212 used in gas or liquid chromatography could have an attached PROM-based ID pod 218 which would contain information about the contents of the column and the kinds of machines and conditions under which it is to be used. When inserted in connector 220, pod 218 would control the use of column 212 (column 212 is inserted in a slot 214 of chromatographic device 200). As with the fluids identification pod of the first embodiment, some of the information stored in pod 218 would be used for identification and control; other information would be displayed (on a display 219) to allow the operator to make effective use of the column.

Referring to FIG. 9, the information stored in pod 218 could include numeric or alphanumeric fields as shown. Information about the column type 230 could include the material (glass, stainless steel), the active packing component (Carbowax 30, ion-exchange resin), and the support component (silica gel, plastic beads). The classes of compounds 232 which can be separated include primary compounds for which the column is very well suited and secondary compounds with which the column will work. The lot number 234 is similar to the lot number in the first embodiment. The date 236 could be the date of manufacture or the date of expiration. The conditions for use 238 could depend on whether the column is for gas chromatography or liquid chromatography. Sample sites 240 could include a range or a maximum. Calibration information 242 could include retention time o standard compound at a given temperature, pressure, flow rate, and other conditions.

As with the first embodiment, the information stored in the PROM can be used to control the operation of the chromatography. In addition, by displaying to the operator information indicating a range of permissible operating conditions or uses (e.g., the primary cluster of compounds or the conditions for use of the column presently installed) the user can operate the device in a manner consistent with the particular chromatograph.

We claim:

1. A fluids pack for use on an analyzer, comprising
   a fluids container,
   fluids held in said container for use in said analyzer,
   an electronic memory device associated with said container and containing (a) information concerning the timing of calibration operations in said analyzer, (b) information uniquely identifying the fluids container, (c) information identifying a class of analyzers, and (d) information identifying a concentration of the fluids,
   said memory device including electrical ports for electrical connection to a memory reader.

2. Apparatus for controlling the operation of an analyzer, comprising
   a fluids container,
   fluids held in said container for use in said analyzer,
   an electronic memory device associated with said container and containing (a) information identifying a class of analyzers, (b) information uniquely identifying the fluids container, (c) information identifying a concentration of said fluids, (d) information identifying a manufacturing lot, and (e) information identifying an expiration date,
   data storage in said analyzer containing (f) information identifying a class of analyzers to which said analyzer belongs and (g) information identifying a current date, and
   circuitry in said analyzer for comparing the class information stored in said data storage with the class information stored in the memory device, for comparing said current date with said expiration date, for controlling the operation of said analyzer based on said concentration information, and for displaying said manufacturing lot information,
   said memory device including electrical ports for electrical connection to a memory reader and said analyzer including a memory reader for electrical connection to said electrical ports.

3. A method for controlling the use of a fluids pack on an analyzer, comprising
   inserting consumable fluids into said pack,
   attaching to said pack an electronic memory device containing (a) information identifying a class of analyzer, (b) information uniquely identifying the fluids container, (c) information identifying a concentration of said fluids, (d) information identifying a manufacturing lot, and (e) information identifying an expiration date,
   storing in a data storage of said analyzer information (f) information identifying a class of analyzers to which said analyzer belongs and (g) information identifying a current date, and
   attaching said pack to said analyzer to enable said analyzer to withdraw fluids from said pack,
   electrically connecting said memory device to said analyzer,
   electrically reading said memory device,
   comparing the class information stored in said analyzer with the class information stored in the memory device,
   determining whether or not to allow said fluid to be withdrawn from said pack based on the results of said comparing
   causing said analyzer to read said unique value from said memory device,
   storing said unique value in said analyzer,
   storing in said analyzer a value indicative of a predetermined number of uses of said pack,
   determining when an actual use has been made of said pack by said analyzer, maintaining in the analyzer a stored number of actual uses of said pack, comparing the predetermined number of uses with the number of actual uses, determining whether or not to allow said fluid to be withdrawn from said pack based on the results of said comparing, causing said analyzer to read said calibration information from said memory, causing said analyzer to perform said calibration at times based on said calibration information, causing said analyzer to display said manufacturing lot to a user, and comparing said expiration date with said current date.

4. A fluids pack for use on a chemistry analyzer, comprising a fluids container, calibration fluids held in said container for use in said chemistry analyzer, and an electronic memory device associated with said container and containing information concerning the timing of calibration operations in said analyzer using said fluids.

5. The fluids pack of claim 4 wherein said memory device also contains information uniquely identifying the fluids container.

6. The fluids pack of claim 4 wherein said memory device also contains information identifying a class of chemistry analyzers.

7. The fluids pack of claim 5 wherein said memory device also contains information identifying a class of chemistry analyzer.

8. The fluids pack of claim 4 wherein said memory device also contains information identifying a concentration of said fluids.

9. The fluids pack of claim 6 or 7 wherein said memory device also contains information identifying a concentration of said fluids.

10. The fluids pack of claim 6 or 9 wherein said memory device also contains information identifying a manufacturing lot.

11. The fluids pack of claim 6 or 9 wherein said memory device also contains information identifying an expiration date.

12. The fluids pack of 4 wherein said memory device includes electrical ports for electrical connection to a memory reader.

13. The fluids pack of claim 12 wherein said memory device also contains information identifying a manufacturing lot, and information identifying an expiration date.

14. Apparatus for controlling the operation of a chemistry analyzer belonging to a class of analyzers comprising a fluids container, fluids held in said container for use in said analyzer, an electronic memory device associated with said container and containing information identifying a class of chemistry analyzers, data storage in said analyzer containing information identifying said class of analyzers to which said analyzer belongs, and circuitry in said analyzer for comparing the class information stored in said data storage with the class information stored in the memory device.

15. The apparatus of claim 14 wherein said memory device also contains information uniquely identifying the fluids container, and said circuitry in said analyzer includes means for comparing it with known valid identifying information.

16. The apparatus of claim 15 wherein said memory device also contains information identifying a concentration of said fluids, and said circuitry in said analyzer includes means for controlling the operation of said analyzer based on said concentration information.

17. The apparatus of claim 15 or 16 wherein said memory device also contains information identifying a manufacturing lot, and said circuitry in said analyzer includes means for displaying said manufacturing lot information.

18. The apparatus of claim 15 or 16 wherein said memory device also contains information identifying an expiration date, and said circuitry in said analyzer includes means for controlling said analyzer on the basis of said expiration information.

19. The apparatus of claim 14 wherein said memory device includes electrical ports for electrical connection to a memory reader, and said analyzer includes a memory reader for electrical connection to said electrical ports.

20. Apparatus for controlling the operation of a chemistry analyzer belonging to a class of analyzers comprising a fluids container, fluids held in said container for use in said analyzer, an electronic memory device associated with said container and containing a unique identifier for said pack, and circuitry in said analyzer for (a) storing said unique identifier, (b) storing information indicative of a predetermined number of uses of said pack, (c) determining when a use has been made of said pack by said analyzer, (d) storing the number of actual uses of said accessory units, and (e) comparing the predetermined number of uses with the number of actual uses.

21. A method for controlling the use of a fluids pack on a chemistry analyzer, comprising inserting consumable fluids into said pack, attaching to said pack an electronic memory device containing information identifying a class of chemistry analyzer, storing in a data storage of said chemistry analyzer information identifying a class of analyzers, attaching said pack to said analyzer to enable said analyzer to withdraw fluids from said pack, electrically connecting said memory device to said analyzer, electrically reading said memory device, comparing the class information stored in said analyzer with the class information stored in the memory device, and determining whether or not to allow said fluid to be withdrawn from said pack based on the results of said comparing.

22. A method for controlling the use of a fluids pack on a chemistry analyzer, comprising associating an electronic memory device with said pack, storing in said memory device a unique value identifying said pack, connecting said pack to said analyzer to enable said analyzer to withdraw fluids from said pack, causing said analyzer to read said unique value from said memory device, storing said unique value in said analyzer, storing in said analyzer a value indicative of a predetermined number of uses of said pack, determining when an actual use has been made of said pack by said analyzer, maintaining in the analyzer a stored number of actual uses of said pack, comparing the predetermined number of uses with the number of actual uses, and determining whether or not to allow said fluid to be withdrawn from said pack based on the results of said comparing.

23. A method for controlling the use of a fluids pack on a chemistry analyzer, comprising associating an electronic memory device with said pack, storing in said memory device a value indicative of a time interval between successive calibrations, connecting said pack to said analyzer to enable said analyzer to withdraw fluids from said pack, causing said analyzer to read said calibration information from said memory, and causing said analyzer to perform said calibration at times based on said calibration information.

24. The method of claim 21, 22, or 23, further comprising storing in said electronic memory device information indicative of the manufacturing lot of said pack, and causing said analyzer to display said manufacturing lot to a user.

25. The method of claim 21, 22, or 23 further comprising storing in said electronic memory device information indicative of an expiration date of said pack, storing in said analyzer a current date, and comparing said expiration date with said current date.

* * * * *